(12) United States Patent
Hinterkopf et al.

(10) Patent No.: US 12,220,571 B2
(45) Date of Patent: Feb. 11, 2025

(54) DEVICE FOR SUPPORTING A TREATMENT USING PULSED ELECTRIC FIELDS IN ORDER TO HEAL WOUNDS AND/OR FOR THE INACTIVATION OF MICROORGANISMS, AND METHOD FOR THE INACTIVATION OF MICROORGANISMS

(71) Applicant: Hinerkopf-Theisen-Mogg Gesellschaft des burgerlichen Rechts, Koblenz (DE)

(72) Inventors: Werner Gerhard Hinterkopf, Bad Ems (DE); Josef Srb, Blatna (CZ); Josef Korous, Blatna (CZ); Jan Hinterkopf, Aachen (DE)

(73) Assignee: Hinerkopf-Theisen-Mogg Gesellschaft des burgerlichen Rechts, Koblenz (DE)

( * ) Notice: Subject to any disclaimer, the term of this patent is extended or adjusted under 35 U.S.C. 154(b) by 161 days.

(21) Appl. No.: 18/004,735

(22) PCT Filed: Jul. 20, 2021

(86) PCT No.: PCT/EP2021/070244
§ 371 (c)(1),
(2) Date: Jan. 9, 2023

(87) PCT Pub. No.: WO2022/018074
PCT Pub. Date: Jan. 27, 2022

(65) Prior Publication Data
US 2023/0248963 A1    Aug. 10, 2023

(30) Foreign Application Priority Data
Jul. 24, 2020 (EP) ..................................... 20187657

(51) Int. Cl.
*A61N 1/04* (2006.01)
*A61N 1/40* (2006.01)

(52) U.S. Cl.
CPC ............. *A61N 1/0468* (2013.01); *A61N 1/40* (2013.01)

(58) Field of Classification Search
None
See application file for complete search history.

(56) References Cited

U.S. PATENT DOCUMENTS

| 4,695,472 A | 9/1987 | Dunn |
| 5,909,086 A | 6/1999 | Kim |

(Continued)

FOREIGN PATENT DOCUMENTS

| CA | 2594284 A1 | 7/2006 |
| GB | 326534 A | 3/1930 |

(Continued)

OTHER PUBLICATIONS

International Preliminary Report on Patentability dated Jan. 24, 2023, of PCT International Application No. PCT/EP2021/070244 filed Jul. 20, 2021.

(Continued)

*Primary Examiner* — Michael W Kahelin
(74) *Attorney, Agent, or Firm* — RAPHAEL BELLUM PLLC

(57) ABSTRACT

The invention relates to a device (10) for supporting a treatment using pulsed electric fields in order to heal wounds and/or for the inactivation of microorganisms. The device (Continued)

comprises an electric energy storage device (16), a pulse generator (17) for providing electric excitation pulses, a transformer (26) for providing high-frequency electric pulses (200) on an output side (28), a first connection of the input side (27) of the transformer (26) being connected to the pulse generator (17), and a treatment instrument (100) which comprises a closed body (102) made of an electrically insulating material and an electrode (110) arranged in the interior of the body (102). A gas or a gas mixture is received in the interior of the body (102), and the treatment instrument (100) is designed to discharge gas in the event of an electric excitation. A first end (103) of the treatment instrument (100) is designed to couple to a first connection of the output side (28) of the transformer (26). Furthermore, a second end (104) of the treatment instrument (100) is designed to contact surfaces and/or biological tissue, and a second connection of the output side (28) of the transformer (26) is connected to a second connection of the input side (27) of the transformer (26) and a housing shielding (13). The housing shielding (13) is electrically insulated from the outer environment by a housing of the device and is thus designed as an ungrounded mass, and the transformer (26) and the pulse generator (17) are designed such that the high-frequency electric pulses (200) have a frequency ranging from 10 kHz to 100 kHz and a pulse repetition rate ranging from 100 kHz to 400 kHz. The invention additionally relates to a method for the inactivation of microorganisms, wherein such a device (10) is provided, and the treatment instrument (100) of the device (10) is excited with high-frequency electric pulses.

13 Claims, 5 Drawing Sheets

(56) References Cited

U.S. PATENT DOCUMENTS

| | | |
|---|---|---|
| 2012/0187841 A1 | 1/2012 | Kittl |
| 2013/0068226 A1 | 3/2013 | Watson |
| 2015/0306411 A1 | 10/2015 | Srb et al. |
| 2016/0030760 A1 | 2/2016 | Srb |

FOREIGN PATENT DOCUMENTS

| | | |
|---|---|---|
| JP | 47-36580 | 11/1972 |
| JP | 2008-539007 | 11/2008 |
| JP | 2015-533529 | 11/2015 |
| WO | 2006/116252 A2 | 11/2006 |
| WO | 2010009103 | 1/2010 |
| WO | 2011/015538 A1 | 2/2011 |
| WO | 2014/094931 A1 | 6/2014 |

OTHER PUBLICATIONS

International Search Report for PCT International Application No. PCT/EP2021/070244, dated Oct. 15, 2021.
Decision to Grant Patent, Japanese Patent Application No. 2023-504720 (whole document).

DEVICE FOR SUPPORTING A TREATMENT USING PULSED ELECTRIC FIELDS IN ORDER TO HEAL WOUNDS AND/OR FOR THE INACTIVATION OF MICROORGANISMS, AND METHOD FOR THE INACTIVATION OF MICROORGANISMS

The invention relates to an apparatus for assisting the healing of wounds and/or for the inactivation of microorganisms, comprising an electrical energy storage unit, a transformer for providing radiofrequency electrical pulses, and a treatment instrument that comprises a body made of an electrically insulating material and an electrode arranged in the interior of the body, a gas or gas mixture being received in the interior of the body and the treatment instrument being configured for a gas discharge in response to electrical excitation. The invention furthermore relates to a method for the inactivation of microorganisms, such an apparatus being provided and the treatment instrument of the apparatus being excited with radiofrequency electrical pulses.

PRIOR ART

In medicine and in other technical fields, it is necessary to disinfect or sterilize objects, such as medical apparatuses, or biological material such as foodstuffs or tissue samples. For sterilization, it is typically required that the number of living microorganisms be reduced by six orders of magnitude. For disinfection, a reduction by five orders of magnitude is typically required.

In the treatment of humans or animals, it may also be necessary to treat, in particular disinfect, tissue such as a skin surface or an open wound, in order to avoid infections and to promote the healing of the wound. Various methods are known for disinfection and sterilization. If an object to be sterilized can withstand elevated temperatures and humidity, sterilization may be carried out in an autoclave. In an autoclave, the object is exposed to hot steam at a temperature of for example 131° C.

Depending on the constitution of the objects or materials to be disinfected, however, it may not be possible to autoclave them. Biological material is destroyed by the action of heat, and various materials used in medical equipment are also insufficiently stable in respect of the conditions prevailing in an autoclave.

Further disinfection methods, in which only minor heating is caused during the disinfection, are also known in the prior art.

U.S. Pat. No. 4,695,472 describes a preserving method and a corresponding apparatus for preserving liquid foodstuffs, in which the foodstuff is exposed to pulses of a strong electric field that has a field strength of from 5 kV/cm to 25 kV/cm and a pulse duration of from 1 µs to 100 µs with a repetition rate of between 0.1 Hz and 100 Hz. The electric field is in this case set up between two electrodes, the foodstuff being fed into a treatment zone between the two electrodes.

WO 2014/094931 A1 discloses an apparatus for treating biological tissue with a low-pressure plasma. The apparatus comprises an electrical energy supply, a transformer for generating a radiofrequency electric field and a probe that can be electrically coupled to the transformer, and a control device for controlling the transformer. A transformer housing is preferably formed as a handle, which allows ergonomic handling of the apparatus, the energy supply being arranged outside the transformer housing. The probe is filled with a noble gas or a noble gas mixture with a pressure of from 500 Pa to at most 3000 Pa. Through excitation of the probe by means of electrical pulses generated using the transformer with a voltage of from 1.8 kV to 35 kV at a frequency of from 10 kHz to 50 kHz and a pulse length of about 250 µs, a low-pressure plasma is generated between the probe and the biological tissue to be treated, the probe being positioned for this purpose at a distance of from 1 mm to 50 mm from the tissue. The biological tissue in this case forms a ground electrode that is connected to a grounding of the voltage source.

The apparatus known from WO2014/094931 A1 may be used to treat tissue of humans or animals, in particular skin surfaces or open wounds. However, promotion of the wound healing extending beyond disinfection of the tissue is not achieved.

WO2011/015538 describes an apparatus for generating a nonthermal atmospheric-pressure plasma. The apparatus comprises a metal housing, which functions as a grounded electrode in the region of the emerging plasma and in which an RF generator, an RF resonance coil having a closed ferrite core suitable for the radiofrequency, an insulating body which functions as a gas nozzle, and a high-voltage electrode mounted in the insulating body are arranged in such a way that the process gas flows around or through them. A radiofrequency at about 1 MHz is used for the excitation.

US 2013/068226 A1 describes an apparatus for providing a cold plasma for inhalation. A biocompatible gas is for this purpose introduced into an apparatus and is exposed to a dielectric barrier discharge. The apparatus has a mask to be worn by a patient, a module for generating the plasma discharge being able to be inserted into a mouth opening.

WO 2006/116252 describes an apparatus for using nonthermal plasmas on living tissue. For this purpose, a plasma is intended to be generated in the vicinity of the tissue without heating the tissue. A distance (plasma gap) is in this case to be maintained between the apparatus and the patient to be treated, in order to generate the cold plasma.

A disadvantage with the known apparatuses and methods for treating tissue with low-pressure plasma is that precise maintaining of the distance between the treatment instrument, or the probe, and the tissue is difficult. Furthermore, the known methods only act superficially, and no effect is achieved in the depth of the tissue. With the known apparatuses and methods based on pulses of high electric fields, it is problematic that two electrodes are needed, between which the treatment zone with the pulsed high electric field is formed. In particular, this makes treatment of large areas of an object considerably more difficult.

It is therefore an object of the invention to provide an apparatus and a method with which inactivation of microorganisms is also achieved in the depth of the tissue. It is furthermore an object of the invention to provide an apparatus with which the healing of wounds can be assisted. In particular, it is an object to carry out stimulation of the four natural phases of wound healing, in order to assist the wound healing. It is also an object of the invention to provide an apparatus which does not require grounding or a second electrode for carrying out the treatment.

SUMMARY OF THE INVENTION

An apparatus for assisting the healing of wounds and/or for the inactivation of microorganisms is proposed, which comprises an electrical energy storage unit, a pulse generator for providing electrical excitation pulses, and a transformer for providing radiofrequency electrical pulses on an output side. In this case, a first terminal of an input side of the transformer is connected to the pulse generator. The apparatus furthermore comprises a treatment instrument that comprises a closed body made of an electrically insulating material and an electrode arranged in the interior of the body, a gas or gas mixture being received in the interior of the body and the treatment instrument being configured for a gas discharge in response to electrical excitation, a first end of the treatment instrument being configured for coupling to a first terminal of the output side of the transformer.

It is furthermore provided that a second end of the treatment instrument is configured for the contacting of surfaces and/or biological tissue, and that a second terminal of the output side of the transformer is connected to a second terminal of an input side of the transformer and to a housing shield, the housing shield being electrically insulated from the surroundings by a housing of the apparatus and therefore being configured as a floating ground, and the transformer and the pulse generator being configured in such a way that the radiofrequency electrical pulses have a frequency in the range of from 10 kHz to 100 kHz. The radiofrequency electrical pulses furthermore preferably have a pulse width in the range of from 1 µs to 1000 µs. A pulse repetition rate of the radiofrequency electrical pulses preferably lies in the range of from 100 Hz to 400 Hz. A pulse-pause ratio preferably lies in the range of from 0.01% to 1%. The treatment instrument is in this case configured to conduct the generated radiofrequency electrical pulses, or the electric fields thereof, to an object to be treated or to an organic or biological material to be treated.

During operation, the electrical pulses excite a gas discharge in the interior of the treatment instrument, the interior of the closed body being filled with a suitable gas. A dielectric displacement current is created in the surroundings of the treatment instrument, the dielectric displacement current being concentrated at the touching location in the event of contact of the treatment instrument with a surface of an object, or of organic material. In this case, provision is made that during operation of the apparatus, the treatment instrument, or the dielectric displacement current existing on the surface of the treatment instrument, is the only outward electrical connection of the apparatus. In particular, the gas received in the closed body is sealed from the surroundings so that the gas discharge is restricted to the interior of the treatment instrument.

In particular, the apparatus has no grounding and contacts the object to be treated only via the treatment instrument. Further electrical connections between the object to be treated and the apparatus are not intended, and are prevented by an electrically insulating housing of the apparatus.

In order to generate the radiofrequency electrical pulses, the apparatus comprises a transformer that transforms electrical excitation pulses with a low voltage into a high voltage. The high voltage is provided on the output side of the transformer, the output side being electrically coupled to the treatment instrument. The low-voltage electrical excitation pulses are provided as a drive signal on an input side of the transformer, for example by a pulse generator or a control unit.

Preferably, the transformer is formed as a pulse-driven resonant transformer with a magnetic core. In such a pulse-driven resonant transformer, a primary coil and a secondary coil are arranged on the common magnetic core. The magnetic core is in this case preferably formed as a ferrite core. In order to provide the radiofrequency electrical pulses, the pulse-driven resonant transformer is excited with the voltage pulses, a repetition rate of the electrical excitation pulses corresponding to the pulse repetition rate of the radiofrequency electrical pulses.

In the pulse-driven resonant transformer with a magnetic core, the primary coil, which represents the input side of the transformer, and the secondary coil, which represents the output side of the transformer, are magnetically coupled to one another via the magnetic core. The secondary coil in this case has a higher number of turns than the primary coil. The primary coil has for example in the range of from 2 to 100 turns, preferably in the range of from 4 to 40 turns. The secondary coil has, for example, in the range of from 1000 to 100 000 turns.

The magnetic core is preferably formed substantially in the shape of a rod, both the primary coil and the secondary coil being wound around the magnetic core.

The length of the magnetic core is preferably from 1 cm to 6 cm. The magnetic core may in this case form chambers in order to receive the individual turns of the coils.

Preferably, the secondary coil is subdivided into a plurality of winding segments that are spaced apart from one another. For example, the magnetic core, which is also used here as a winding core onto which the secondary coil and the primary coil are wound, may provide a plurality of coil compartments, the windings in one of the coil compartments respectively representing a winding segment of the secondary coil. For example, from 2 to 20, preferably from 2 to 15 winding segments may be provided. Particularly preferably, from 3 to 9 winding segments are provided. Each winding segment may, for example, have from 100 to 1000 turns of the secondary coil.

The primary coil may also be subdivided into a plurality of segments. For example, the primary coil may be arranged in the form of from 1 to 5 winding segments on the magnetic core used as a common winding core, the individual segments of the primary coil being spatially separated from one another, for example by providing a plurality of coil compartments on the winding core.

Particularly preferably, the primary coil is arranged between the winding segments of the secondary coil on the magnetic core. In this case, the primary coil may for example be configured in the form of a single segment and may therefore be arranged entirely between two winding segments of the secondary coil. Alternatively, the primary coil likewise has a plurality of winding segments, a winding segment of the primary coil respectively being arranged between two winding segments of the secondary coil.

A copper wire is preferably used as the wire for the winding of the coils, the diameter for the copper wire of the secondary coil preferably being in the range of from 0.01 mm to 0.1 mm, particularly preferably in the range of from 0.03 mm to 0.07 mm. A thicker copper wire, which preferably has a diameter from three to 10 times greater than the copper wire used for the secondary coil, is preferably used for the primary coil.

The frequency of the generated radiofrequency electrical pulses is substantially determined by a resonant frequency of the oscillating system formed by the secondary coil of the pulse-driven transformer and the treatment instrument. In particular, the resonant frequency is determined by the inductance of the secondary coil, a capacitance of the coil and the capacitance of the treatment instrument. The excitation of this oscillating system with the electrical excitation pulses is preferably matched to this resonant frequency. A fine adjustment of the excitation of the pulse-driven transformer is preferably carried out by shifting the placement of the primary coil in relation to the secondary coil. Furthermore, in particular, an electrical capacitance may be modified by the selection of the distances between the individual winding segments and of the number of winding segments, so that the natural frequency or resonant frequency can be influenced. In particular, it is in this case preferred to vary the distances of the winding segments between two adjacent segments of the secondary coil.

The pulse-driven transformer and the treatment instrument are configured in such a way that the natural frequency, or resonant frequency, of the oscillating system formed on the output side of the transformer lies in the range of from 10 kHz to 100 kHz, preferably in the range of from 20 kHz to 80 kHz, and particularly preferably in the range of from 30 kHz to 70 kHz.

In this case, account is preferably taken of the fact that this resonant frequency given substantially by the inductance of the secondary coil and the capacitance of the treatment instrument shifts when the treatment instrument touches an object. By an object being touched with the treatment instrument, the electrical capacitance of the oscillating system changes, which correspondingly leads to a change in the frequency.

For example, the treatment instrument and the transformer are configured in such a way that a radiofrequency electrical pulse with a frequency of from 60 kHz to 70 kHz is created on the output side in response to excitation with an electrical excitation pulse in the form of a DC voltage pulse of for example 25 V with a duration of for example 9 µs when the treatment instrument is not in contact with an object. The generated radiofrequency electrical pulse has its greatest amplitude directly after the excitation with the electrical excitation pulse, and then decays because of the damped oscillation. The pulse width of the radiofrequency electrical pulse is substantially longer than the duration of the electrical excitation pulse.

If the treatment instrument is touched by a person, for example, the electrical capacitance of the oscillating system on the output side of the transformer changes. For example, the resonant frequency of the oscillating system on the output side of the pulse-driven transformer is about 40 kHz.

The pulse width of the electrical excitation pulses, that is to say the time duration of an electrical excitation pulse, preferably lies in the range of from 0.1 µs to 20 µs, particularly preferably in the range of from 0.5 µs to 15 µs, and more particularly preferably in the range of from 1 µs to 10 82 s. For example, the pulse duration is 9 µs.

The pulse repetition rate, which determines how many electrical excitation pulses are generated per second, lies in the range of from 100 Hz to 400 Hz. Preferably, the pulse repetition rate is in the range of from 200 Hz to 300 Hz, and the pulse repetition rate is for example 280 Hz. The pulse repetition rate of the electrical excitation pulses corresponds to the pulse repetition rate of the radiofrequency electrical pulses.

The pulse width of the radiofrequency electrical pulses, that is to say the time duration of a radiofrequency electrical pulse, lies in the range of from 1 µs to 1000 µs, preferably in the range of from 50 µs to 500 µs, and particularly preferably in the range of from 100 µs to 250 µs. The pulse width is determined in particular by a damping of the oscillation, excited by the electrical excitation pulse, of the oscillating system formed by the transformer and the treatment instrument.

The pulse-pause ratio is determined by the selected pulse width, or pulse duration, and the pulse repetition rate of the radiofrequency electrical pulses. This pulse-pause ratio, also referred to as a duty cycle or duty factor, gives the ratio between the pulse width and the subsequent pause until the emission of the next electrical pulse. The pulse-pause ratio lies in the range of from 0.01% to 1%, preferably in the range of from 0.05% to 0.5% and particularly preferably in the range of from 0.1% to 0.25%. With a pulse duration of for example 9 µs and a repetition rate of for example 250 Hz, the pulse-pause ratio is 0.225%.

Preferably, a control unit that drives the transformer via the pulse generator with low-voltage electrical excitation pulses, or the drive signal, is provided. The voltage of the electrical excitation pulses lies, for example, in the range of from 10 V to 70 V and is transformed by the transformer into the high voltage, or the radiofrequency electrical pulses. Particularly preferably, the voltage lies in the range of from 15 V to 40 V. The repetition rate of the electrical excitation pulses in this case corresponds to the pulse repetition rate of the radiofrequency electrical pulses. The pulse duration of the electrical excitation pulses, on the other hand, is substantially less than the pulse width of the radiofrequency electrical pulses. In particular, the duration of the electrical excitation pulses is preferably shorter than the pulse width of the radiofrequency electrical pulse at least by a factor of 5, particularly preferably at least by a factor of 10.

The high voltage of the radiofrequency electrical pulses preferably lies in the range of from 5 kV to 40 kV. Particularly preferably, the high voltage lies in the range of from 10 to 25 kV. These specifications in this case refer to the maximum peak-to-peak voltage of the radiofrequency electrical pulses.

Preferably, the apparatus is configured to limit a current on the output side of the transformer to a maximum value in the range of from 1 µA to 300 µA. Particularly preferably, the current on the output side is limited to a maximum value in the range of from 10 µA to 120 µA. For example, the maximum current is limited to 100 µA. Means, for example an electrical resistance, a fuse or a monitoring or safety device, which for example measures the current directly or indirectly and interrupts the supply of current if a limit value is exceeded, may be used to limit the maximum current.

By the proposed parameters for the radiofrequency electrical pulses that are generated on the output side of the transformer and are forwarded to the treatment instrument coupled to the output side of the transformer, limitation of the emitted power is achieved. It is therefore sufficient to monitor compliance with these parameters, that is to say in particular the voltage and frequency of the radiofrequency electrical pulses.

Limiting the emitted power of the apparatus ensures that excessive heating of objects or biological material, which is treated with the apparatus, is avoided. In particular for application on a human or an animal, heating needs to be restricted in such a way that the skin is heated by at most 3° C. within 10 minutes. For application on a human, furthermore, heating to above a temperature of 41° C. must not take place.

Preferably, the apparatus comprises a safety device that is configured to monitor the electrical parameters on the output side of the transformer and to interrupt an energy supply to the transformer if predetermined limit values for one of the electrical parameters are exceeded or fallen below.

The monitored electrical parameters on the output side are preferably selected from the electrical current, the voltage, the pulse repetition rate, the pulse width, the pulse frequency and combinations of at least two of these parameters. For example, the voltage and frequency are monitored. Preferably, all the aforementioned electrical parameters are monitored.

Preferably, limit values are defined for the monitored electrical parameters, the energy supply to the transformer being interrupted if an upper limit value is exceeded or a lower limit value is fallen below. The limit values may, for example, be specified as a percentage deviation. The deviation allowable in this case is preferably at most 5% and particularly preferably at most 3%. For a setpoint repetition rate of 280 Hz, for example, a deviation of +/−5% may be specified, so that shutdown takes place in the event of a repetition rate of more than 294 Hz or less than 266 Hz.

The safety device preferably comprises corresponding sensors in order to record the respective electrical parameters. In particular, a time-resolved measurement of the voltage may in this case take place, further electrical parameters such as (peak) voltage, frequency, pulse width or pulse length, pulse-pause ratio and pulse repetition rate being determined therefrom by digital processing. A current sensor may furthermore be provided in order to measure the current.

Means for measuring the voltage at the primary coil or at the secondary coil are preferably configured with high impedance in order to load the voltage source, which likewise has a high impedance, as little as possible. The means may, in particular, comprise an analog/digital converter in order to measure the voltage. An evaluation of the measurement result, and in particular a comparison with predetermined limit values, may then for example be carried out by means of a computer program which is executed by a suitable processor, for example a microcontroller.

A measurement on the secondary side of the transformer may, for example, be carried out by measuring a voltage at a capacitor that is connected to the output side of the transformer by means of a diode, an impedance converter and a voltage divider. The impedance converter may for example be configured as an operational amplifier, and the voltage divider may be produced by means of resistors or by means of capacitors.

Preferably, a measurement of the voltage and/or the frequency of the radiofrequency electrical pulse is carried out during an excitation pause of the resonant transformer by means of a measurement of the voltage induced on the primary side of the resonant transformer. In this way, direct measurements on the high-voltage side of the transformer are not necessary. In this case, for example, the voltage applied to the primary coil during the excitation pause may be measured directly.

A particularly simple measurement for checking the voltage may, for example, be carried out by using the voltage induced on the primary side by oscillations in the resonant transformer to charge a capacitor via a diode. Preferably, the connection to the primary coil is in this case carried out by means of an impedance converter and optionally by means of a voltage divider. By means of a controllable switch, which is configured for example as a MOSFET, the output of the impedance converter may be short-circuited to the housing shield and therefore to the second terminal of the primary coil during the electrical excitation pulse, so that the excitation pulse cannot charge the capacitor. Only after the end of the excitation of the transformer is the controllable switch turned off so that the positive half-waves of the oscillation existing in the transformer respectively charge the capacitor. The voltage measurable at the capacitor is representative of the voltage on the output side, that is to say at the secondary coil, of the transformer. The impedance converter may for example be configured as an operational amplifier, and the voltage divider may be produced by means of resistors or by means of capacitors.

Additionally or alternatively, the apparatus preferably comprises a safety device that is configured to detect an electrical connection of the apparatus to a power supply system and, if such a connection exists, to interrupt an energy supply to the transformer. The effect achieved by this is that there is no connection between the apparatus and a power supply system during operation and a risk to users due to the power supply voltage during the operation of the apparatus is therefore precluded.

Preferably, the apparatus has a housing in the form of a handle, the electrical energy storage unit, the transformer and a part of the treatment instrument being accommodated in the housing. Another part of the treatment instrument protrudes from the housing. Particularly preferably, the housing is configured in such a way that all the components of the apparatus except for the part of the treatment instrument protruding from the housing are accommodated in the housing.

The housing preferably has an outer housing case that is made of an electrically insulating material. The material of the housing case is, in particular, a plastic.

The housing preferably comprises an electrical shield, which is formed as a housing shield, is arranged on an inner side of the housing case and is electrically conductive. Preferably, the shield is configured in the form of an electrically conductive foil and/or in the form of electrically conductive plates, or in the form of an electrically conductive coating of the inner side of the housing case. For example, an electrically conductive foil, for example aluminum foil, is used as the shield.

The electrical shield preferably encloses the apparatus fully, openings in the shield only being provided for the treatment instrument protruding from the housing and optionally for terminals and/or control elements.

The housing shield is fully insulated by the housing, so that no conductive outward connection takes place from the housing shield. In particular, no conductive connection takes place between the housing shield and a person who guides the apparatus for a treatment of an object, and no conductive connection takes place between the housing shield and the object to be treated.

Preferably, the apparatus comprises a charging terminal, by means of which the electrical energy storage unit of the apparatus can be charged. Preferably, the electrical energy storage unit is configured as a rechargeable battery, for example as a lithium ion battery or as a nickel metal hydride battery. It is furthermore conceivable to configure the electrical energy storage unit as a capacitor, for example a supercapacitor.

The apparatus preferably comprises at least one control element, by means of which the apparatus can be turned on and/or off. In addition, a control element by means of which the power of the apparatus can be selected may be provided. The control element is, for example, configured as an on/off switch or as a button.

The control element or elements are preferably connected to a control unit of the apparatus.

The control unit of the apparatus preferably comprises the pulse generator for providing a drive signal, or the electrical excitation pulses, delivered to the input side of the transformer. For this purpose, the control unit possesses a connection to the electrical energy storage unit. As an alternative thereto, the control unit and the pulse generator may also be configured as separate components.

The pulse generator is, for example, configured as a voltage source that is turned on and off in a controlled way by using a semiconductor switch, for example a MOSFET.

In this case, for example, the semiconductor switch is turned on for the time duration of the excitation pulse and is turned off in the subsequent excitation pause.

The pulse generator may alternatively, for example, be configured as an arbitrary function generator by means of which any desired signal waveforms can be generated. The control unit may furthermore comprise an amplifier in order to amplify the electrical excitation pulses generated by the pulse generator.

Provision may be made to configure the control unit and the safety device as a common unit. As an alternative thereto, the control unit and the safety device are configured as separate units.

The treatment instrument of the apparatus is used to conduct the generated radiofrequency electrical pulses, or the electric fields thereof, to the object to be treated or to the organic or biological material to be treated. The treatment instrument comprises a closed body made of an electrically insulating material and an electrode arranged in the interior of the body. A gas or gas mixture is received in the interior of the body of the electrode, and the treatment instrument is configured for a gas discharge in response to electrical excitation by the electrical pulses. During operation of the apparatus, the received gas is excited by means of a gas discharge. The electric fields, or a resulting dielectric displacement current, may therefore be induced starting from the electrode through the excited gas onto the body of the treatment instrument. The dielectric displacement current, or the electric fields, can then be transmitted onto an object that the treatment instrument touches.

The treatment instrument has a first end, which is configured for coupling to the output side of the transformer, and has a second end which is configured for the contacting of surfaces of objects and/or of biological tissue.

The body of the treatment instrument is preferably shaped substantially elongately, provision being made for the second end to have larger dimensions than the first end.

The electrically insulating material of the body of the treatment instrument is preferably a glass. The glass is preferably selected in such a way that it is suitable for contact with injured skin of a patient. This means that the glass must not release any toxic substances and must not trigger any irritations or allergies. Suitable glasses are for example borosilicate glass, quartz glass or soda-lime glass.

The treatment instrument preferably comprises a current feed-through and an end cap at the first end, which is configured for coupling to the output side of the transformer. The end cap is preferably made of a plastic. The plastic is preferably selected from polytetrafluoroethylene (PTFE), polyethylene (PE), polystyrene (PS), polyethylene (PE), polypropylene (PP), polyamide (PA) and acrylonitrile butadiene styrene (ABS) copolymer, polypropylene being particularly preferred.

The plastic of the end cap is preferably reinforced with fibers, the fibers preferably being selected from glass fibers, carbon fibers and aramid fibers, glass fibers being particularly preferred. The fiber volume fraction of the fibers preferably lies in the range of from 20% to 50% and particularly preferably in the range of from 30% to 40%. Furthermore, long fibers are preferred to short fibers. Fibers having a length in the range of from 1 mm to 50 mm are to be regarded as long fibers.

Shorter fibers involve short fibers, and longer fibers involve endless fibers.

The current feed-through provided at the first end of the treatment instrument has an electrical contact on an outer side and establishes an electrical connection to the electrode in the interior of the body of the treatment instrument.

The electrode is preferably arranged next to the first end in the interior of the body of the treatment instrument, and is preferably configured in the shape of a pin.

The pin shape of the electrode preferably has a length in the range of from 10 mm to 13 mm, a length in the range of from 11 mm to 12 mm being particularly preferred. A diameter of the electrode preferably lies in the range of from 0.1 to 3 mm, particularly preferably in the range of from 0.5 mm to 2 mm. For example, the diameter of the electrode is 1 mm.

The material of the electrode is preferably a metal. The metal is in this case preferably selected from copper, stainless steel, nickel, titanium, platinum and corresponding alloys. The electrode may furthermore be coated.

Preferably, there is a connecting region with a first diameter next to the first end of the treatment instrument and there is preferably a bulb region with a second diameter next to the second end of the treatment instrument, the second diameter being greater than the first diameter and the bulb region occupying at least one third of the total length of the bulb.

Preferably, the volume of the bulb region occupies at least two thirds of the total volume of the treatment instrument.

Preferably, the body of the treatment instrument comprises precisely two regions, namely the bulb region and the connecting region, which need not merge abruptly into one another but may be connected via a continuous transition. The bulb region preferably has a length of from 40 mm to 80 mm, a length of from 50 mm to 60 mm being preferred. For example, the bulb region has a length of 58 mm. The diameter of the bulb region is preferably in the range of from 15 mm to 25 mm, preferably from 18 mm to 22 mm, and is for example 20 mm.

The second end of the body is preferably configured to be substantially planar, so that a circular surface closes the bulb region. This surface may merge via a continuous transition or via a sharp edge into the cylindrical bulb region.

For contact with an object to be treated, or with organic material to be treated, both the substantially planar surface and the curved wall of the bulb region may be used.

The connecting region of the body of the treatment instrument preferably has a length of from 30 mm to 60 mm, a length of from 40 mm to 50 mm being preferred. For example, the bulb region has a length of 45 mm. The diameter of the connecting region is preferably in the range of from 5 mm to 15 mm, preferably from 8 mm to 12 mm, and is for example 10 mm.

The end cap encloses the body of the treatment instrument at the first end, an electrical contact surface remaining free at the first end. The end cap preferably comprises a sleeve region that extends over at least a part of the connecting region starting from the first end. The length of the sleeve region is preferably in the range of from 10 mm to 50 mm, particularly preferably in the range of from 15 to 30 mm. For example, the sleeve region is 20 mm long. The diameter of the end cap is preferably in the range of from 7 mm to 18 mm, preferably from 10 mm to 15 mm. For example, the diameter of the end cap is 12 mm.

The end cap is preferably connected to the body of the treatment instrument by means of an adhesive that is arranged in the sleeve region. The adhesive is preferably a thermally stable epoxy resin adhesive.

The body of the treatment instrument is closed so that it is gas-tight. The body of the treatment instrument is filled with a noble gas or a noble gas mixture that has a reduced pressure in relation to the atmospheric pressure of normally about 1 bar. The pressure of the gas fill of the treatment instrument preferably lies in a range of from 0.001 mbar to 1 mbar, particularly preferably in the range of from 0.01 to 0.7 mbar.

The treatment instrument may, for example, be filled with a noble gas such as neon or argon or a mixture of a plurality of noble gases. The gas mixture may also contain further gases, for example nitrogen, for example a mixture of neon, argon and nitrogen. Neon is preferably used for the gas fill. With neon, for example, higher field strengths of the electric and magnetic fields are achieved in comparison with filling with argon.

The body of the treatment instrument is preferably configured with one wall, so that only a single layer of glass separates the interior of the treatment instrument, which is filled with the noble gas or the noble gas mixture, from the surroundings.

The treatment instrument of the apparatus is preferably configured to be replaceable, in order to be able to change or clean it when required. By separating the treatment instrument, it can in particular also be sterilized easily.

Preferably, the apparatus comprises a safety device that detects the presence of the treatment instrument and, in the absence of the treatment instrument, interrupts an energy supply to the transformer. For this purpose, the safety device may comprise a detector, which is configured for example as a microswitch or as a photoelectric barrier. A detector formed as a microswitch is, for example, arranged in such a way that it is activated in the presence of a treatment instrument. A detector formed as a photoelectric barrier is, for example, arranged in such a way that a light beam is interrupted by the treatment instrument when it is present. An end cap of the treatment instrument may in this context, in particular, be configured to be opaque in order to interrupt the light beam of the photoelectric barrier.

Preferably, the treatment instrument has a data memory that can be read by a reader of the apparatus when a treatment instrument is fitted into the apparatus. The data memory may, for example, be formed optically in the form of a one-dimensional barcode or in the form of a matrix code such as a QR code. As an alternative thereto, the data memory may for example be formed as a memory chip that can be read by means of a wireless communication method such as RFID.

The data memory of the treatment instrument may, for example, contain indications of the type and/or the required operating parameters as well as indications of limit values to be complied with. Compliance with the limit values may then, in particular, be checked by a correspondingly configured safety device. The limit values to be complied with may, in particular, contain upper limits and/or lower limits for voltage, frequency and/or current strength of the radiofrequency electrical pulses.

In order to permit simple and reliable cleaning of the treatment instrument by autoclaving with steam, the treatment instrument is preferably configured to withstand steam at a temperature in the range of from 110° C. to 140° C. The materials used, that is to say in particular the glass of the body and the plastic of the end cap, and optionally used connecting means, for example an adhesive, are selected accordingly. Compared with conventional end caps made of a metal, the proposed end cap made of a plastic material has favorable thermal properties and a good resistance to hydrolysis.

In order to ensure simple electrical coupling of the treatment instrument, the treatment instrument is preferably received by means of a plug-in connector, the treatment instrument being electrically connected to the output side of the transformer by means of a contact of the plug-in connector. The contact of the plug-in connector is, for example, configured as a spring contact that is prestressed against the electrical contact surface of the treatment instrument when the treatment instrument is fitted.

Preferably, the treatment instrument has a sleeve region that at least partially encloses the connecting region of the treatment instrument, and the plug-in connector has a clamping device that is configured to hold the treatment instrument on the sleeve region.

A further aspect of the invention relates to a method for the inactivation of microorganisms, wherein one of the apparatuses described is provided and the treatment instrument of the apparatus is excited with radiofrequency electrical pulses. It is furthermore provided that the treatment instrument is applied onto a surface of an object in which microorganisms are intended to be inactivated, so that the body of the treatment instrument touches the surface, and the treatment instrument is guided over the surface of the object. In this case, the housing shield of the apparatus is electrically isolated from the object so that no electrically conductive connection is established between the object and the second terminals of the transformer.

In particular, the apparatus and the object in which microorganisms are intended to be inactivated are not connected to a common ground, and the object is contacted during the method only with a single electrode, which in this case is the body of the treatment instrument of the apparatus.

The described apparatuses are preferably configured for use with the methods described here, so that features described in connection with the methods also apply correspondingly for the apparatuses, and vice versa features described in the context of the apparatuses apply for the methods.

Preferably, the object is selected from medical instruments and organic or biological material. The organic material is, for example, skin or a tissue sample. Correspondingly, the method may in particular be used for nontherapeutic treatments.

The method is also suitable for use on a patient, for example in order to inactivate microorganisms in the region of wounds and/or to assist the healing of wounds. Because of infection with germs, the problem often arises that wounds heal poorly. If this involves a germ that is resistant to one or more antibiotics, the treatment of the wound is often particularly difficult and time-consuming. If the proposed method is used, even resistant germs are killed and wound healing is promoted. For use in the treatment of a wound, the proposed apparatus is provided and the treatment instrument of the apparatus is excited with radiofrequency electrical pulses. The treatment instrument is then preferably brought in direct contact with the skin, or the wound, so that the treatment instrument touches the patient and is guided one or more times over the entire surface of the wound, each region of the surface of the wound preferably being in direct contact with the treatment instrument in the range of from one minute to 10 minutes, particularly preferably in the range of from 2 to 6 minutes. The electrical parameters of the radiofrequency electrical pulses are, for example, for this purpose selected as follows: 20 kV voltage (peak-to-peak), 55 kHz frequency, 280 Hz repetition rate and 128 µs pulse width.

As an alternative thereto, it is possible to cover the wound to be treated or to leave an already applied dressing in place during the treatment and therefore not remove it. For a treatment of the wound, the treatment instrument of the apparatus is in this case placed directly onto a wound covering or the dressing, so that it touches the wound covering or the dressing, and is guided one or more times over the entire surface of the wound. The wound covering may, for example, be a conventional wound compress. The electrical parameters of the radiofrequency electrical pulses are, for example, for this purpose selected as follows: 29 kV voltage (peak-to-peak), 55 kHz frequency, 280 Hz repetition rate and 156 µs pulse width.

During the treatment of wounds, the apparatus may be guided either by a patient who is to be treated or by another person. During the treatment of tissue samples that have been taken, or other organic or biological material, a corresponding procedure is carried out.

The method is furthermore suitable, in particular, for the sterilization or disinfection of medical instruments. For this purpose, the proposed apparatus is provided and the treatment instrument of the apparatus is excited with radiofrequency electrical pulses. The treatment instrument is then brought in direct contact with the surface of the medical instrument to be disinfected, so that the treatment instrument touches the medical instrument directly and is guided one or more times over the entire surface of the instrument, each region of the surface preferably being in direct contact with the treatment instrument in the range of from one minute to 10 minutes, particularly preferably in the range of from 2 to 6 minutes. For the disinfection of any other desired objects or articles, a corresponding procedure is carried out. The electrical parameters of the radiofrequency electrical pulses are, for example, for this purpose selected as follows: 34 kV voltage (peak-to-peak), 55 kHz frequency, 280 Hz repetition rate and 170 µs pulse width.

It is assumed that the effect due to the treatment instrument is based on the action of the electric fields. The electric fields, and the dielectric displacement currents due to the latter, not only act on the surface that is in contact with the treatment instrument but also act in the underlying material, so that the object is also treated, and microorganisms are inactivated, in the interior.

It is assumed that the effect of the treatment instrument on germs, for example bacteria, is based on a cell membrane of the bacteria being permanently damaged by the pulsed electric fields. Bacteria that are present on the surface of or inside an object are damaged during the treatment with the apparatus and consequently killed. In this case, the object is not substantially heated and is not exposed to a significant dose of UV radiation either, so that the method works very noninvasively.

It has furthermore been observed that, during the treatment of a wound with the described apparatus, the wound healing is promoted to an extent that goes beyond the purely disinfecting effect. It is assumed that the dielectric displacement currents emanating from the treatment instrument stimulate the wound healing processes.

The electric fields emanating from the treatment instrument are influenced by material that lies in the vicinity. In this case, the electric fields are concentrated in particular by the presence of electrically conductive materials. For a particularly good effect on small portable objects, it is therefore preferred for them to be held in the hand by a person who is carrying out the treatment, while the treatment instrument is guided over the surface of the object. The body of the operator has a high electrical conductivity, and therefore ensures that the electric fields are advantageously concentrated on the object held in the hand.

The electric fields created on the surface of the treatment instrument during the electrical excitation of the treatment instrument preferably have a field strength in the range of from 500 V/m to 6000 V/m, particularly preferably in the range of from 500 V/m to 1800 V/m.

A magnetic flux density on the surface of the treatment instrument lies, for example, in the range of from 10 µT to 73 µT, preferably in the range of from 10 µT to 43 µT.

In Vitro Tests

The effect of the apparatus, or the method, on test germs was studied. As test germs, a) NCTC 12493 *Staphylococcus aureus* and b) ATCC 27853 *Pseudomonas aeruginosa* were studied. For this purpose, a procedure similar to the zone of inhibition test for testing the sensitivity of a bacterium to an antibiotic was carried out. The respective test germ was for this purpose applied onto an agar medium and the agar medium was subsequently treated or not treated with the method according to the invention. The success of the treatment is clearly visible by an inhibition of the growth of the germs in comparison with the untreated agar medium.

The test germ a) NCTC 12493, *Staphylococcus aureus*, is a spherical gram-positive bacterium. Staphylococci do not move actively and do not form spores. *Staphylococcus aureus* is very widespread, occurs in many habitats, and usually lives as a harmless saprobiont and commensal belonging to the normal colonization flora of the skin and mucous membrane in humans, although it may also be pathogenic and, besides skin and soft tissue infections, also cause pneumonia, meningitis, endocarditis, and even a toxic shock syndrome and sepsis.

The test germ b) ATCC 27853 *Pseudomonas aeruginosa* (from the Latin aerugo, verdigris) is a gram-negative, oxidase-positive rod-shaped bacterium of the genus *Pseudomonas*. It was discovered in 1900 by Walter Migula. The nomenclature is due to the blue-green coloration of the pus in the event of purulent infectious diseases.

The test germs are important hospital germs that have also developed resistances to several antibiotics.

The test germs were respectively applied onto prepared agar plates with a diameter of 70 mm, in order to simulate a wound with wound exudate. The agar plates were then treated by using the described apparatus with the parameters specified in Table 1. The treatment duration was varied as indicated in Table 2, no treatment being carried out for the comparative tests 5 and 6. During the specified treatment duration, the treatment instrument of the apparatus was placed onto the agar plate and moved over the surface of the agar plate. During the treatment time, the treatment instrument was in contact with the surface of the agar plate for the whole time. The agar plates were then treated in an incubator for at least 48 hours. After 48 hours, a first evaluation was carried out. Depending on the result, a further treatment was carried out in the incubator for a further 48 hours.

In order to detect a colony, the surface of the agar plates is streaked with a sterile annular loop and the loop of wire is subsequently assessed.

In the tests, the apparatus was operated with the following parameters:

TABLE 1

| Parameter | Value |
| --- | --- |
| Voltage (peak-to-peak on the output side): | 23 kV |
| Frequency on the output side: | 25.9 kHz (upon contact of the treatment instrument with the object) 60 kHz (no contact) |

TABLE 1-continued

| Parameter | Value |
| --- | --- |
| Pulse repetition rate: | 300 Hz |
| Maximum current on the output side | 80 µA |

The test results are listed in Table 2.

TABLE 2

| No. | Germ | Treatment duration | Result after 48 h | Result after 96 h |
| --- | --- | --- | --- | --- |
| 1 | a) | 2 min | zone of inhibition about 30% | about 30% |
| 2 | b) | 2 min | zone of inhibition about 40% | about 40% |
| 3 | a) | 6 min | zone of inhibition about 90% | about 90% |
| 4 | b) | 6 min | zone of inhibition about 90% | about 90%* |
| 5 | a) | (untreated) | no zone of inhibition | no zone of inhibition, colonized area even larger |
| 6 | b) | (untreated) | no zone of inhibition | no zone of inhibition, colonized area even larger |

The % specifications indicated in the "Result" column refer to the percentage of the area of the agar plate that had no bacterial colonization and therefore a zone of inhibition. In Tests 3 and 4, almost complete inhibition of the bacterial growth was achieved. The remaining colonized area of 10% or less of the total area of the agar plate is attributed to the fact that the treatment instrument has not fully swept over the edges of the plate because of the walls of the Petri dish used. In Tests 3 and 4, complete inhibition of the bacterial growth for the surface of the agar plate treated with the treatment instrument is therefore assumed.

In Tests 1 and 2, complete inhibition of the bacterial growth was not achieved. This is attributed to the fact that the short treatment duration of only 2 minutes was not sufficient for complete sweeping over the entire surface of the agar plate, and large regions of the agar plate were therefore not treated by sweeping over with the treatment instrument.

In order to test the compatibility for use on the human body as well, heating of the skin was studied. For this purpose, the treatment instrument was placed onto the skin of a test subject in the region of the hand and was excited with electrical pulses according to the parameters in Table 1. The heating of the skin was monitored by means of an infrared thermometer. The starting temperature before the beginning of the treatment was 32° C. After 6 minutes of constant skin contact, the temperature rose by 1° to 33° C. The guidelines required for medical products, namely an increase of not more than 5° and not above 41° C., are complied with and not even nearly reached.

For the compatibility, a study was also conducted of whether UV radiation is produced to an impermissible extent during the gas discharge in the treatment instrument. In a test with the parameters specified in Table 1, a UV power of 0.035 mW/cm$^2$ was measured directly next to the bulb region of the treatment instrument. The guideline of 0.1 mW/cm$^2$ was complied with.

In the tests on the test subject, no harmful effect of the treatment instrument on human cells could be detected.

Use of the Apparatus on Burn Wounds

For a patient with burn wounds in the region of the scalp, the chin (neck-thorax), the chest and the hands, the burn wounds were initially treated conventionally. The affected skin areas, head-neck-thorax and chest as well as both hands, had IIb to III degree burns.

There was a tangential necrectomy on all the affected skin areas. The wounds on the hands and lower arms were subsequently treated by means of debridement and split thickness skin grafting from the thighs. For the chest, debridement and Integra grafting were carried out on both sides. The face and head were treated with a moist dressing.

Apart from the burn wounds on the head and on the neck, the course of healing was good, or normal. During stationary rehabilitation directly following this, conservative treatment was continued by means of ointment dressings containing dexpanthenol.

The status of the patient after three months of conventional treatment was as follows:

After unsuccessful wound closure on the head and an inflamed neck wound, the wound treatment started to be assisted by using the described apparatus. At this point in time, the wound in the region of the scalp was not closed. The wound in the region of the chin had inflammation with suppuration. The wounds in the hands were closed, but the wounds were cracked and the scar tissue was not smooth.

The wounds in the region of the scalp and the chin region were respectively treated in the morning and afternoon 3 times for 2 minutes with the apparatus according to the invention. The wounds were covered with a gauze compress before the treatment. The treatment instrument of the apparatus was subsequently brought in direct contact with the gauze compress and guided over the region of the wound so that the entire area of the wound was treated. In this case, the treatment instrument was not moved for about 30 seconds after placement onto the wound, or the compress.

After about 30 seconds, the treatment instrument was guided over the wound for about 15 seconds. The treatment instrument was subsequently placed onto the wound again with a new focus and then guided over the wound again for about 15 seconds. The 2-minute treatment was repeated 3 times.

During the first and second treatments, the treatment was carried out with level 4 of the apparatus, the electrical parameters used for the radiofrequency electrical pulses being as follows: 20 kV voltage (peak-to-peak), 45 kHz frequency, 280 Hz repetition rate.

During the third treatment, the treatment was carried out with level 2 of the apparatus, the electrical parameters used for the radiofrequency electrical pulses being as follows: 9.5 kV voltage (peak-to-peak), 45 kHz frequency, 280 Hz repetition rate.

The burn wound in the region of the scalp had already closed almost fully after 8 days of treatment.

The treatment was continued, the next 14 days respectively one treatment in the morning and one in the evening without one compress with level 2.

The wound in the neck region was fully healed after 21 days.

The wound on the scalp was treated for a further 30 days with level 2, one treatment being carried out daily. In special cases, for example in order to clean the wound after a shower, level 4 was used. After the next 30 days (about three months) of the treatment, not only was the wound in the region of the scalp fully closed but hair growth surprisingly took place, so that the function of the scalp was fully restored. It is assumed that the alternating electric and/or magnetic fields emanating from the treatment instrument triggered the biological effect in the dermis inter alia of re-stimulating the hair growth, and revived the overlying epidermis in such a way that hair could grow from the burn wound.

The wound in the chin region was free of inflammation after 8 days of treatment, and although still slightly visible after 23 days of treatment it was otherwise fully healed.

The wounds in the region of the hands were already closed at the start of treatment, so that no wound covering was necessary for the treatment with the apparatus according to the invention. The treatment instrument of the apparatus was brought in direct contact with the wounds for the treatment, each finger being treated once daily for 2 minutes. The treatment was assisted by applying a medical skin cream.

After three months of treatment, the grafts are fully functional and the scars are smooth. Internal scarring did not occur.

The respective steps were always carried out with a sterile treatment instrument from sterile packaging. After the treatment, the treatment instruments were cleaned and, vacuum-packed in packaging after cleaning, sterilized in an autoclave at 141° C. The treatment instruments were thus always stored sterilely and therefore sterilely usable.

BRIEF DESCRIPTION OF THE DRAWINGS

Embodiments of the invention will be explained in more detail with the aid of the drawings and the following description.

EMBODIMENTS OF THE INVENTION

In the following description of the embodiments of the invention, elements which are the same or similar are denoted by the same references, repeated description of these elements being omitted in certain cases. The figures represent the subject-matter of the invention only schematically.

Figure 1A:
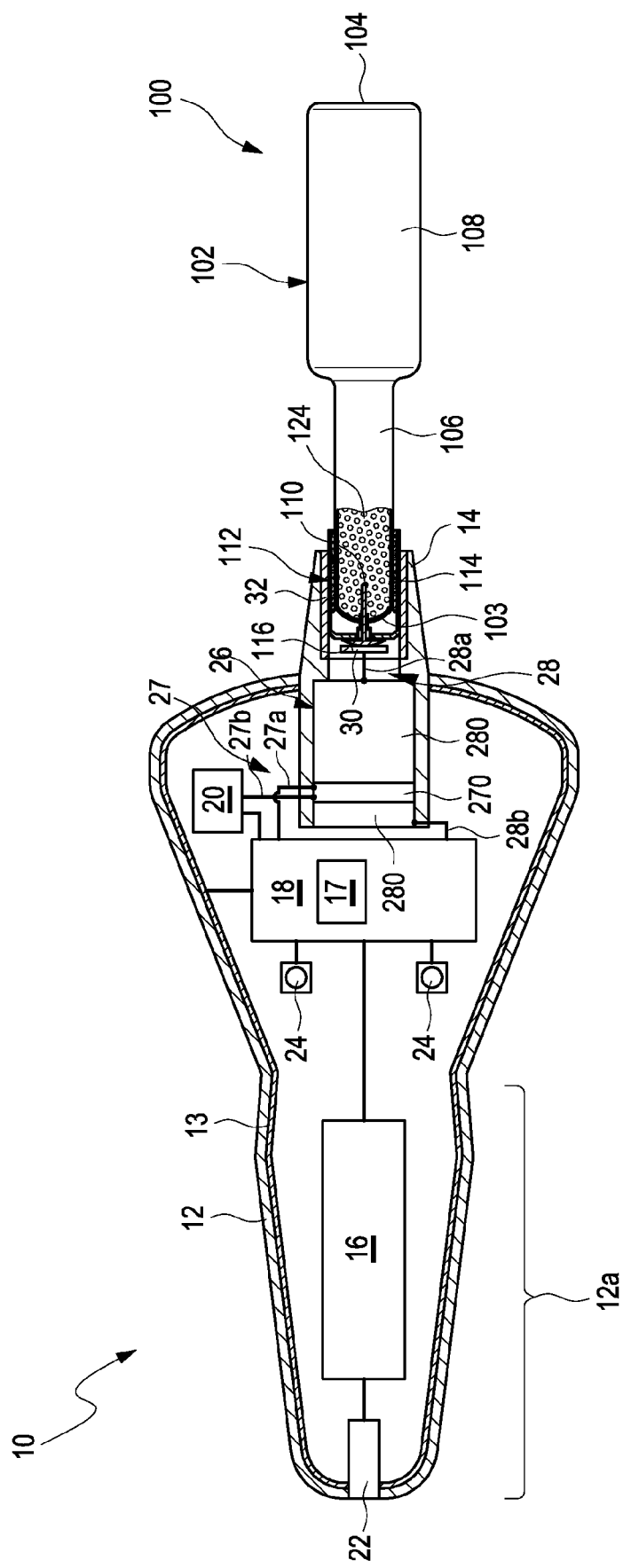
FIG. 1a shows a schematic representation of the apparatus for assisting the healing of wounds and/or for the inactivation of microorganisms as a sectional view from above.

FIG. 1a shows an apparatus 10 for assisting the healing of wounds and/or for the inactivation of microorganisms. The apparatus 10 comprises a housing 12 that accommodates all the components of the apparatus 10 except for a part of a treatment instrument 100. At the location where the treatment instrument 100 protrudes from the housing 12, an instrument guide 14 is provided. The housing 12 with the instrument guide 14 is made of an electrically insulating material, for example a plastic. In the example shown in FIG. 1a, the housing 12 of the apparatus 10 is provided with a handle section 12a on which the apparatus 10 can be held ergonomically in the hand during a treatment.

The apparatus 10 comprises an electrical energy storage unit 16, which supplies a controller 18 with electrical energy. The electrical energy storage unit 16 is preferably configured as a lithium ion battery. In order to charge the electrical energy storage unit 16, a charging terminal 22 that is accessible through an opening in the housing 12 is provided.

The controller 18 is connected to the input side 27 of a transformer 26. During operation of the apparatus 10, by using a pulse generator 17, the controller 18 generates electrical excitation pulses that are delivered to the input side 27 of the transformer 26. The transformer 26 then generates a high voltage in the form of radiofrequency electrical pulses, which are emitted on an output side 28 of the transformer 26. The high voltage is used in order to excite the treatment instrument 100, which is electrically coupled to the transformer 26. A housing shield 13, which in the example represented is configured in the form of an electrically conductive foil on the inner side of the housing 12, is arranged for electrical shielding of the components accommodated in the housing 12. Alternatively, the housing shield 13 may for example also be configured as an electrically conductive coating of the inner side of the housing 12.

The schematic representation of the transformer 26 shows that a primary coil 270 is inserted between two parts of a secondary coil 280. A first terminal 27a of the input side of the transformer 26, that is to say of the primary coil 270, is in this case connected directly to the controller 18 and therefore to the pulse generator 17. A second terminal 27b of the primary coil 270 is connected via a safety device 20 to the controller 18 and is connected via the controller 18 to the housing shield 13. A first terminal 28a of the output side of the transformer 26, that is to say of the secondary coil 280, is connected to the treatment instrument 100. A second terminal 28b of the secondary coil 280 is connected to the controller 18, and via the latter to the housing shield 13. The second terminals 27b and 28b are in this case respectively connected indirectly via the controller 18 to the housing shield 13, and therefore have the same electrical potential. The electrical ground formed by the housing shield 13 is not grounded, but is electrically isolated by the housing 12.

The treatment instrument 100 comprises a body 102 made of an electrically insulating material. The body 102 is in this case configured elongately, and has a connecting region 106 and a bulb region 108. The material of the body 102 is, for example, a glass. There is a first end 103 of the treatment instrument 100 next to the connecting region 106 and a second end 104 of the treatment instrument 100 next to the bulb region 108. The bulb region 108 protrudes entirely from the housing 12 of the apparatus 10, while the connecting region 106 is at least partially enclosed by the housing 12. The interior of the body 102 is filled with a noble gas 124, which has a reduced pressure in comparison with the ambient pressure.

Next to the first end 103, the treatment instrument 100 has an end cap 112, which is made of a plastic. The end cap 112 has a sleeve region 114 that encloses a part of the connecting region 106 next to the first end 103. An electrical contact surface 116, which is electrically connected through the end cap 112 and the body 102 to an electrode 110, is furthermore arranged at the first end 103.

The treatment instrument 100 is received replaceably in the apparatus 10. For this purpose, a clamping apparatus 32 is provided, which receives the treatment instrument 100 at the sleeve region 114 of the end cap 112. In this position, the electrical contact surface 116 of the treatment instrument 100 is contacted with an electrical spring contact 30, which is connected to the output side 28 of the transformer 26. The treatment instrument 100 is therefore electrically coupled to the transformer 26 when the treatment instrument 100 is received in the clamping apparatus 32 of the apparatus 10.

In order to turn the apparatus 10 on and/or off and in order to make it possible to change operating parameters, control elements 24 that are connected to the controller 18 are provided. The control elements 24 are, for example, configured as buttons. After the apparatus 10 is turned on, the controller 18 starts to generate low-voltage electrical excitation pulses, which are delivered to the transformer 26 as a control signal on the input side 27 of the latter. The electrical excitation pulses are transformed by the transformer into high-voltage radiofrequency electrical pulses and used as an excitation signal for the excitation of the treatment instrument 100. In this case, the noble gas 124 received in the interior of the body 102 of the treatment instrument 100 is excited into a gas discharge. Furthermore, high alternating electric fields are created.

The function of the apparatus 10 is preferably monitored. For this purpose, the apparatus 10 in the embodiment represented in FIG. 1a comprises a safety device 20, which in this embodiment is configured as an additional component. As an alternative thereto, the safety device 20 may also be configured as part of the controller 18. The safety device 20 is configured and adapted to monitor the high voltage on the output side 28 of the transformer 26, that is to say the radiofrequency electrical pulses, in respect of predetermined limit values for electrical parameters not being fallen below or exceeded. The electrical parameters comprise for example the electrical current, the voltage, a pulse repetition rate, a pulse width and a pulse frequency. In the embodiment represented in FIG. 1a, the measurement is carried out on the input side 27 of the transformer 26, use being made of the fact that, after the decay of the electrical excitation pulse, the radiofrequency electrical pulses generate a signal on the input side 27 of the transformer 26, which can be measured. For a measurement of these electrical parameters, in the example represented the second terminal 27b of the input side 27 of the transformer 26 is connected via the safety device 20 to the controller 18. If the limit values are exceeded or fallen below, the energy supply to the transformer 26 is interrupted by the controller 16. As an alternative or in addition, it is possible to monitor the electrical parameters on the output side of the transformer 26. In this case, for example, the first terminal 28a of the output side 28 has an additional connection to the safety device 20.

Figure 1B:
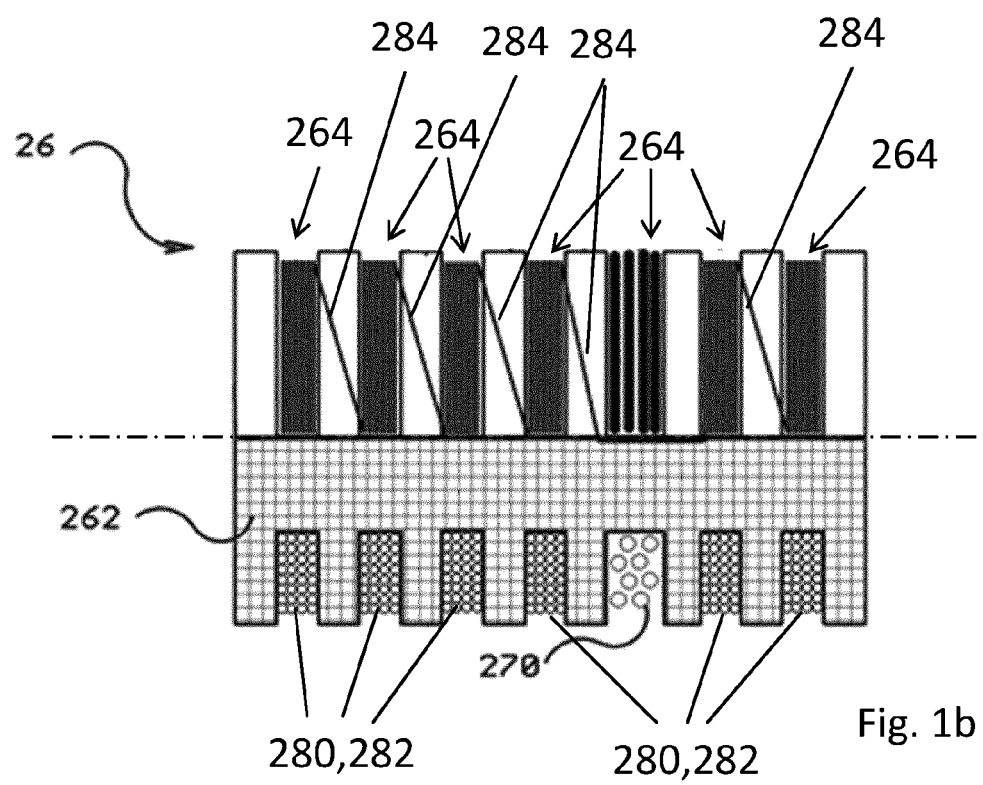
FIG. 1b shows a schematic sectional view of a transformer.

FIG. 1b shows a schematic sectional view of the transformer 26 configured as a resonant transformer. The view is in two parts, the upper half showing a plan view and the lower half showing a sectional view of the transformer 26. The transformer 26 has a core 262, which in the example represented in FIG. 1b has seven coil compartments 264.

In the example represented, the secondary coil 280 of the transformer 26 is divided into six coil segments 282, one of the coil segments 282 respectively being arranged in one of the coil compartments 264. The individual coil segments 282 are arranged at a distance from one another by the coil compartments 264. Electrically, the individual coil segments 282 are connected in series, two coil segments 282 arranged next to one another respectively being electrically connected to one another by a connection 284. Because of the distance respectively between two of the coil segments 282, an electrical capacitance is in each case formed, which influences the natural frequency or resonant frequency of the oscillating system on the output side 28, cf. FIG. 1a, of the transformer 26. Correspondingly, this resonant frequency may be adjusted by changing the distances.

In the example represented, the primary coil 270 is configured as a single segment, which is likewise arranged in one of the coil compartments 264. In this case, the primary coil 270 is located between two coil segments 282 of the secondary coil 280.

Figure 2:
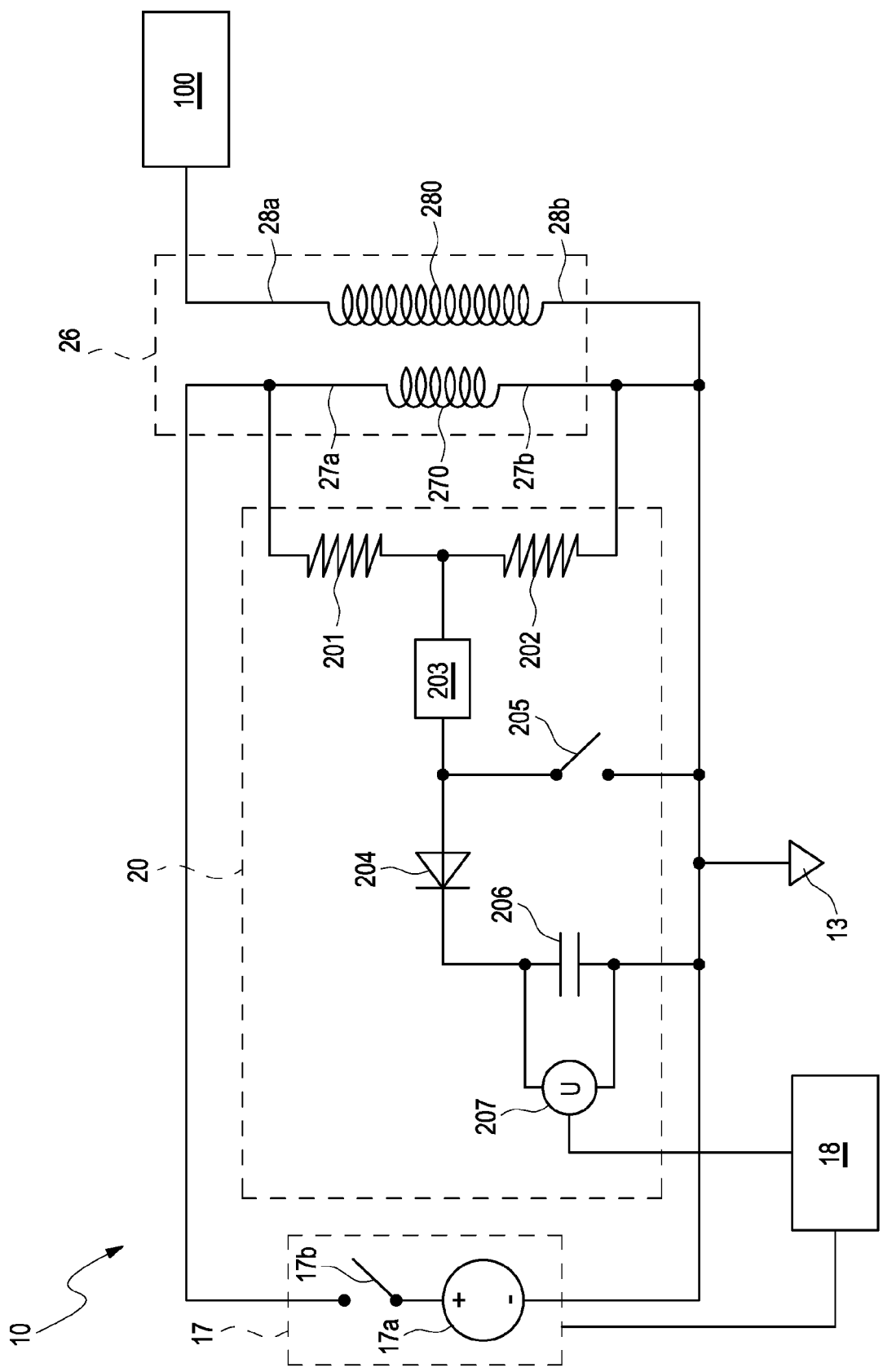
FIG. 2 shows a simplified schematic circuit diagram of the apparatus.

FIG. 2 shows a simplified schematic circuit diagram of the apparatus 10. In this case, in particular, the way in which the safety device 20 is connected to the transformer 26 in order to measure electrical parameters is represented. The transformer 26 is configured as a pulse-driven transformer and has a primary coil 270 and a secondary coil 280. A first terminal 27a of the input side 27, or of the primary coil 270, is connected to the pulse generator 17. A second terminal 27b of the input side 27, or of the primary coil 270, is connected to the housing shield 13. A first terminal 28a of the output side 28, or of the secondary coil 280, is connected to the treatment instrument 100 and a second terminal 28b of the output side 28, or of the secondary coil 280, is likewise connected to the housing shield 13.

In the simplified representation of FIG. 2, the pulse generator 17 comprises a DC voltage source 17a, which is connected via the switch 17b to the transformer 26 for the duration of an electrical excitation pulse.

In the embodiment of FIG. 2, the schematically represented safety device 20 is configured to determine electrical parameters of the radiofrequency electrical pulses by means of a measurement of the voltage induced in the primary coil by these radiofrequency electrical pulses. For this purpose, the safety device 20 is connected to the first and second terminals 27a, 27b of the primary coil 270.

The safety device 20 checks the electrical parameters of the radiofrequency electrical pulses by means of the measurement of a voltage at a capacitor 206, which is charged by a current induced in the primary coil 270. For this purpose the capacitor 207 is connected, via a diode 204 and an impedance converter 203 and a voltage divider formed by a first resistor 201 and a second resistor 202, to the first terminal 27a of the primary coil 270. By means of a controllable switch 205, which is for example configured as a MOSFET, the output of the impedance converter 203 can be short-circuited to the housing shield 13, and therefore to the second terminal 27b of the primary coil 270, during the electrical excitation pulse so that the electrical excitation pulse cannot charge the capacitor 206. Only after the end of the excitation of the transformer 26 is the controllable switch 205 turned off so that the positive half-waves of the oscillation existing in the transformer 26 respectively charge the capacitor 206. The voltage applied to the capacitor 206 may then be measured by voltage measuring means 207. The controller 18 may then control the pulse generator 17 as a function of the result of the voltage measurement, and for example turn the pulse generator 17 off if predetermined limit values are exceeded or fallen below.

In the representation of FIG. 2, the pulse generator 17, the safety device 20 and the controller 18 are represented as separate components. Provision may, however, be made to configure several or all of these components as a common unit, as is indicated in FIG. 1a.

Figure 3:
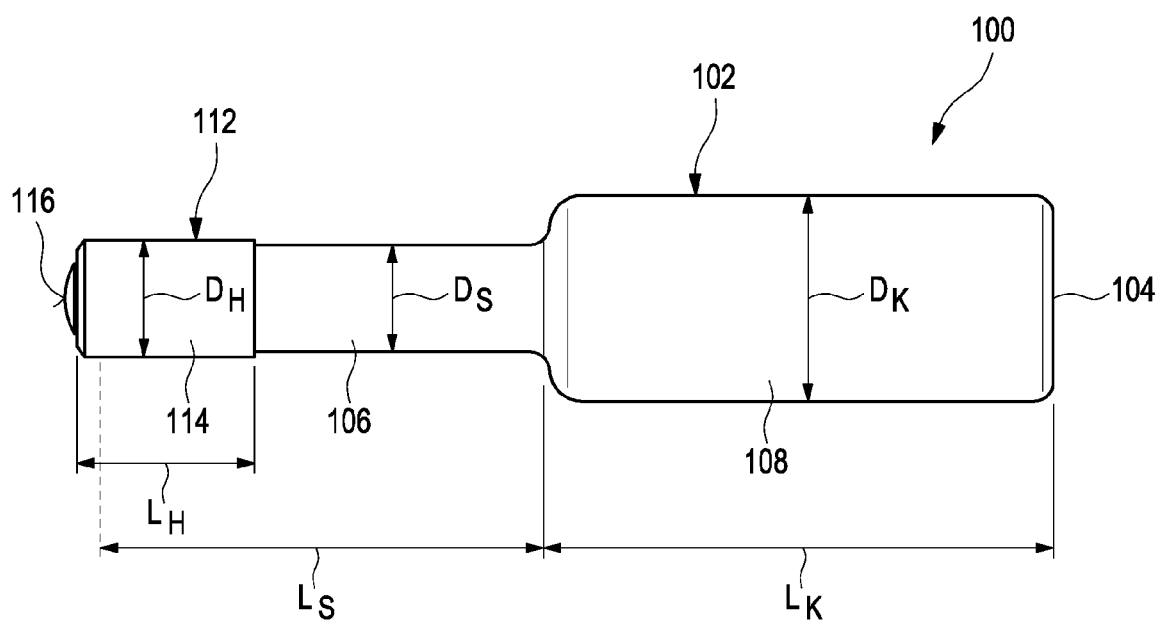
FIG. 3 shows a schematic representation of a treatment instrument of the apparatus.

The treatment instrument 100 of the apparatus 10 is schematically represented in FIG. 3.

The treatment instrument 100 comprises a body 102, which is made of an electrically insulating material, for example glass.

Next to the first end 103 of the treatment instrument 100, there is the connecting region 106, which has a first diameter $D_S$, and next to the second end 104 of the treatment instrument 100 there is the bulb region 108, which has a second diameter $D_K$. The second diameter $D_K$ is in this case greater than the first diameter $D_S$. The connecting region 106 has a first length $L_S$, and the bulb region 108 has a second length $L_K$. The first length $L_S$ of the connecting region 106 occupies about 45% of the total length of the body 102 in the embodiment represented.

Preferably, the volume of the bulb region 108 occupies at least two thirds of the total volume of the body 102 of the treatment instrument 100.

As may be seen from the representation of FIG. 3, the bulb region 108 and the connecting region 106 do not merge abruptly into one another. The body 102 has a continuous transition between the connecting region 106 and the bulb region 108.

In the embodiment represented, the second end 104 of the body 102 of the treatment instrument 100 is configured to be substantially planar, so that a circular surface closes the bulb region 108. This surface merges via a continuous transition into the cylindrical bulb region 108. For contact with an object to be treated, or with organic material to be treated, both the substantially planar surface and the curved wall of the bulb region 108 may be used.

The end cap 112 encloses the body 102 of the treatment instrument 100 at the first end 103, an electrical contact surface 116, cf. FIGS. 1 and 3, remaining free at the first end 103. The end cap 112 comprises a sleeve region 114, which extends over at least a part of the connecting region 106 starting from the first end. The sleeve region 114 has a length $L_H$ and a diameter $D_H$.

Figure 4:
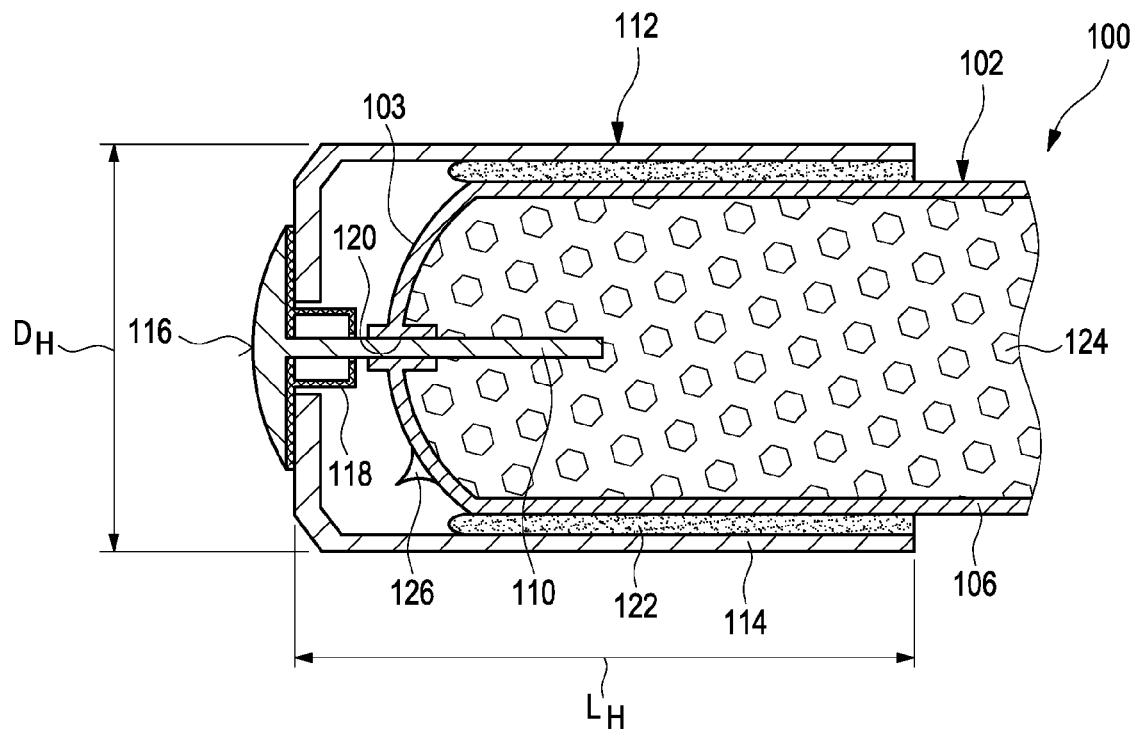
FIG. 4 shows a detail view of the treatment instrument.

FIG. 4 shows a detail view of the treatment instrument 100, which shows the part next to the first end 103 in a sectional view. It may be seen that the end cap 112 encloses the body 102 of the treatment instrument 100 at the first end 103, an electrical contact surface 116 contacting the electrode 110 in the interior of the body 112 through the end cap 112. Between the electrical contact surface 116 and an electrical feed-through 120 through the body 102, in the embodiment shown in FIG. 3 there is a rivet 118 made of an electrically insulating material, which surrounds an electrical connection between the electrical feed-through 120 and the electrical contact surface 116.

It may furthermore be seen in FIG. 4 that the end cap 112 covers an evacuation opening 126 of the body 102. Through the evacuation opening 126, during the production of the body 102, air was initially evacuated and a noble gas 124, for example neon, was subsequently introduced into the interior of the body 102. The evacuation opening 126 was then closed.

The end cap 112 furthermore comprises the sleeve region 114, which extends over at least a part of the connecting region 106 starting from the first end 103. The sleeve region 114 has a length $L_H$ and a diameter $D_H$. In order to fasten the end cap 112 on the body 102, in the embodiment represented in FIG. 3 an epoxy adhesive 122 is used, which is arranged between the body 102 and the sleeve region 114 of the end cap 112.

Figure 5:
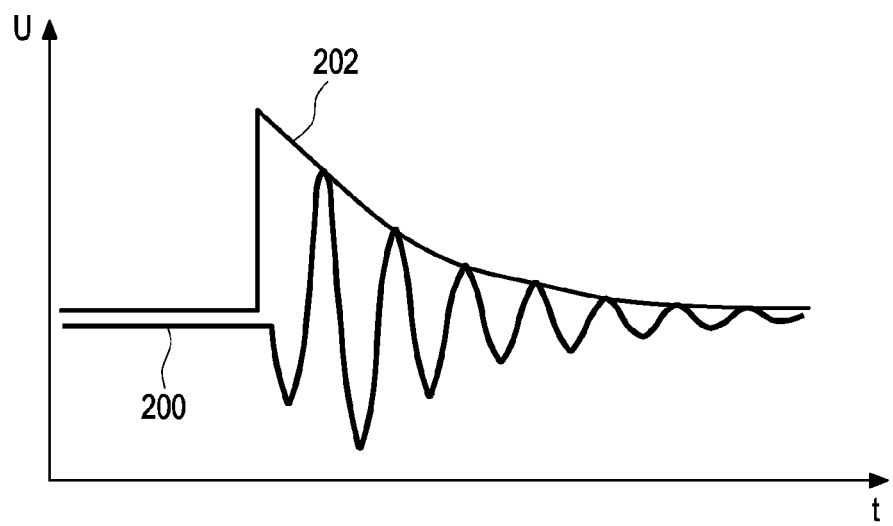
FIG. 5 shows a qualitative representation of a radiofrequency electrical pulse.
Figure 6:
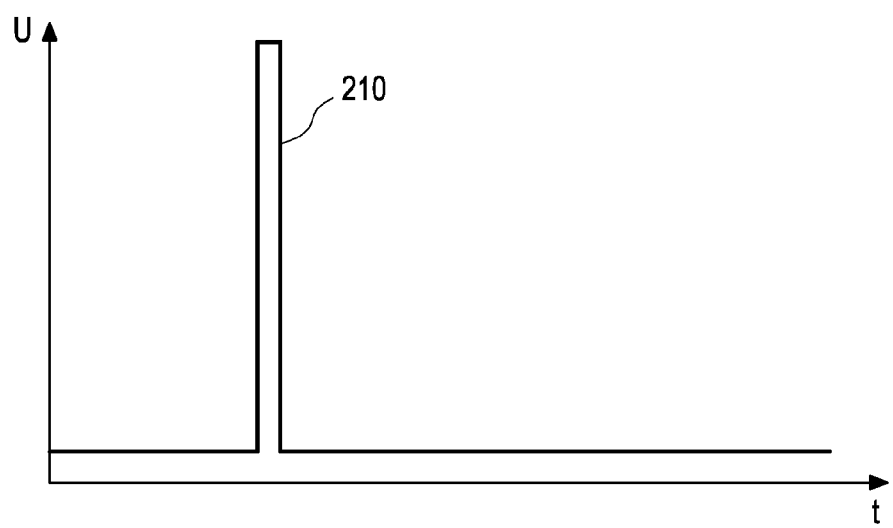
FIG. 6 shows a qualitative representation of an electrical excitation pulse for the excitation of the transformer.

FIG. 5 shows the qualitative profile of a radiofrequency electrical pulse 200 on the output side 27 of the transformer 26. The radiofrequency electrical pulse 200 is created after an excitation pulse 210, which is represented in FIG. 6 and is generated by the pulse generator 17 of the controller 18, has been applied to the transformer 26. The excitation pulse 210 excites the transformer 26 configured as a resonant transformer, cf. FIG. 1a, into oscillation, so that a high-voltage radiofrequency signal that is used as a radiofrequency electrical pulse 200 for the electrical excitation of the treatment instrument 100 is generated.

In FIGS. 5 and 6, the voltage is plotted on the Y axis and the time is plotted on the X axis. The excitation pulse 210 shown in FIG. 6 is, for example, obtained by a DC voltage being turned on and off again by means of a semiconductor switch, for example a MOSFET. FIGS. 5 and 6 respectively show a single pulse.

The radiofrequency electrical pulse 200 represented in FIG. 5 has an envelope 202 that follows an exponential decay in the example shown. A pulse width, or pulse duration, of the radiofrequency electrical pulse 200 may be defined here as the time until the decay of the envelope 202 has fallen to a value of A/e, where A is the maximum amplitude and e is Euler's number.

The invention is not restricted to the exemplary embodiments described here and the aspects highlighted therein. Rather, many variants that lie within the capacity of the person skilled in the art are possible within the scope specified by the claims.

LIST OF REFERENCES 10 apparatus
12 housing
12a handle section
13 housing shield
14 instrument guide
16 electrical energy storage unit
17 pulse generator
17a voltage source
17b switch
18 controller
20 safety device
201 first resistor
202 second resistor
203 impedance converter
204 diode
205 switch
206 capacitor
207 voltage measuring means
22 charging terminal
24 control element
26 transformer
262 core
264 coil compartment
27 input side
27a first input side terminal
27b second input side terminal
270 primary coil
28 output side
28a first output side terminal
28b second output side terminal
280 secondary coil
282 coil segment
284 connection
30 electrical spring contact
32 clamping device
100 treatment instrument
102 body
103 first side
104 second side
106 connecting region
108 bulb region
110 electrode
112 end cap
114 sleeve region
116 electrical contact surface
118 rivet 120 electrical feed-through
122 epoxy adhesive
124 noble gas
126 evacuation opening
200 radiofrequency electrical pulse
202 envelope
210 excitation pulse
D diameter (S=connecting region, H=sleeve region, K=bulb region)
L length (S=connecting region, H=sleeve region, K=bulb region)

The invention claimed is:

1. A device (10) for supporting a treatment with pulsed electric fields for wound healing and/or for inactivating microorganisms, comprising
an electrical energy storage (16),
a pulse generator (17) for providing electrical excitation pulses,
a transformer (26) for providing high-frequency electrical pulses (200) at an output side (28), wherein a first terminal of an input side (27) of the transformer (26) is connected to the pulse generator (17), and
a treatment instrument (100) comprising a body (102) made of an electrically insulating material and an electrode (110) arranged inside the body (102),
wherein a gas or gas mixture is accommodated inside the body (102) and the treatment instrument (100) is configured for gas discharge upon electrical excitation,
wherein a first end (103) of the treatment instrument (100) is configured for coupling to a first terminal of the output side (28) of the transformer (26),
wherein a second end (104) of the treatment instrument (100) is configured to contact surfaces and/or biological tissue, and that a second terminal of the output side (28) of the transformer (26) is connected to a second terminal of an input side (27) of the transformer (26),
wherein the transformer (26) and the pulse generator (17) are configured in such a way that the high-frequency electrical pulses (200) have a pulse repetition rate in the range from 100 Hz to 400 Hz,
wherein the treatment instrument (100) is configured to conduct the generated high-frequency electric pulses (200) or their electric fields to an object to be treated or to an organic or biological material to be treated,
wherein said body (102) is a closed body (102),
wherein the device comprises a housing and a housing shield (13) to which said second terminal of the output side (28) of the transformer (26) is connected,
wherein the housing shield (13) is electrically insulated from the outside world by a housing of the device (10) and thus is configured as a floating ground,
wherein the pulse generator (17) is configured in such a way that the high-frequency electrical pulses (200) have a frequency in the range from 10 kHz to 100 KHz.

2. The device (10) according to claim 1, wherein the device (10) further comprises a safety device (20) which is configured to measure a voltage and/or a frequency of the high-frequency electrical pulses (200) at the output side (28) of the transformer (26) and to interrupt a power supply to the transformer (26), if a voltage and/or a frequency of the high-frequency electrical pulses (200) exceed and/or fall below predetermined limit values and/or which is configured to recognize an electrical connection of the device (10) to a power supply system and to interrupt a power supply to the transformer (26) if such a connection is present.

3. The device (10) according to claim 1, wherein the transformer (26) is designed as a pulse-driven transformer and is excited with excitation pulses (210) for providing the high-frequency electrical pulses (200), wherein a repetition rate of the excitation pulses (210) corresponds to the pulse repetition rate of the high-frequency electrical pulses (200).

4. The device (10) according to claim 3, further configured in that an excitation of the pulse-operated transformer is adjustable by shifting the position of the primary coil of the transformer with respect to the secondary coil of the transformer.

5. The device (10) according to claim 2, wherein the measurement of the voltage and/or frequency of the high-frequency electrical pulses (200) during an excitation pause of the pulse-driven transformer is carried out via a measurement of the voltage induced at the primary side of the pulse-driven transformer.

6. The device (10) according to claim 1, wherein the treatment instrument (100) has a current feedthrough for the electrode (110) at the first end (103) and the current feedthrough comprises an end cap (112) made of a plastic.

7. The device (10) according to claim 6, wherein the plastic of the end cap (112) is reinforced with fibers.

8. The device (10) according to claim 1, wherein the body (102) of the treatment instrument (100) is filled with a noble gas (124) or a noble gas mixture with a pressure in the range of 0.001 mbar to 7 mbar.

9. The device (10) according to claim 1, wherein a bar region (106) with a first diameter $D_s$ adjoins the first end (103) of the treatment instrument (100) and a piston region (108) with a second diameter $D_k$ adjoins the second end (104) of the treatment instrument (100),
wherein the second diameter $D_k$ is larger than the first diameter $D_s$ and
wherein the piston region (108) takes up at least one third of the total length of the body (102).

10. The device (10) according to claim 6, wherein the end cap (112) has a sleeve region (114) which at least partially encloses the bar region (106) of the treatment instrument (100), and in that the treatment instrument (100) is held on the sleeve region (114) via a clamping device (32).

11. The device (10) according to claim 1, wherein the treatment instrument (100) is configured for autoclaving with steam at a temperature in the range from 110° C. to 140° C.

12. A method for inactivating microorganisms, comprising:
providing a device (10) according to claim 1 and exciting the treatment instrument (100) of the device (10) with high-frequency electrical pulses (200),
placing the treatment instrument (100) on a surface of an object in which microorganisms are to be inactivated, so that the body (102) of the treatment instrument (100) touches the surface, and guiding the treatment instrument (100) over the surface of the object,
wherein the housing shield (13) is electrically separated from the object so that no electrically conductive connection is established between the object and the second terminals (27b, 28b) of the transformer (26),
wherein the object is selected from medical instruments and organic material, and
wherein the organic material is a tissue sample.

13. The method according to claim 12, wherein the method comprises inactivating microorganisms inside the object.

* * * * *

UNITED STATES PATENT AND TRADEMARK OFFICE
CERTIFICATE OF CORRECTION

| | | |
|---|---|---|
| PATENT NO. | : 12,220,571 B2 | Page 1 of 1 |
| APPLICATION NO. | : 18/004735 | |
| DATED | : February 11, 2025 | |
| INVENTOR(S) | : Werner Gerhard Hinterkopf et al. | |

It is certified that error appears in the above-identified patent and that said Letters Patent is hereby corrected as shown below:

On the Title Page

At item "(71) Applicant", replace:
"Hinerkopf-Theisen-Mogg Gesellschaft des burgerlichen Rechts"
With:
--Hinterkopf-Theisen-Mogg Gesellschaft des burgerlichen Rechts--

At item "(73) Assignee", replace:
"Hinerkopf-Theisen-Mogg Gesellschaft des burgerlichen Rechts"
With:
--Hinterkopf-Theisen-Mogg Gesellschaft des burgerlichen Rechts--

Signed and Sealed this
Third Day of June, 2025

Coke Morgan Stewart
*Acting Director of the United States Patent and Trademark Office*